(12) United States Patent
Kallenbach et al.

(10) Patent No.: US 10,660,999 B2
(45) Date of Patent: May 26, 2020

(54) PUMP, AND METHOD FOR OPERATING A PUMP FOR FLUIDS

(71) Applicant: Berlin Heart GmbH, Berlin (DE)

(72) Inventors: Sebastian Kallenbach, Kassel (DE); Aaron Rodemerk, Potsdam (DE); Daniel Strommenger, Ludwigsfelde (DE); Adrian Wisniewski, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 142 days.

(21) Appl. No.: 15/565,623

(22) PCT Filed: Apr. 12, 2016

(86) PCT No.: PCT/EP2016/058039
§ 371 (c)(1),
(2) Date: Oct. 10, 2017

(87) PCT Pub. No.: WO2016/166114
PCT Pub. Date: Oct. 20, 2016

(65) Prior Publication Data
US 2018/0071443 A1   Mar. 15, 2018

(30) Foreign Application Priority Data

Apr. 13, 2015   (EP) .................................. 15163311

(51) Int. Cl.
*A61M 1/10* (2006.01)
*A61M 1/12* (2006.01)

(52) U.S. Cl.
CPC ........ *A61M 1/1086* (2013.01); *A61M 1/1015* (2014.02); *A61M 1/1031* (2014.02);
(Continued)

(58) Field of Classification Search
CPC .............. A61M 1/1086; A61M 1/1031; A61M 1/1015; A61M 1/101; A61M 1/122
(Continued)

(56) References Cited

U.S. PATENT DOCUMENTS 5,725,357 A    3/1998  Nakazeki et al.
6,048,363 A *  4/2000  Nagyszalanczy ... A61M 1/1086
                                                        415/900

(Continued)

FOREIGN PATENT DOCUMENTS

EP          0 971 212 A1   1/2000

*Primary Examiner* — Brian T Gedeon
*Assistant Examiner* — Philip C Edwards
(74) *Attorney, Agent, or Firm* — Brinks Gilson & Lione

(57) ABSTRACT

Methods for operating a pump are provided, the pump comprising a rotor for conveying fluids, wherein the volume flow rate through the pump and the pressure difference across the pump is determined, wherein at least one first operating parameter and in particular a second operating parameter of a first group of operating parameters are detected and, depending on the value of the first and in particular also the value of a second operating parameter of the first group, the volume flow rate through the pump and the pressure difference across the pump is determined from detected values of the operating parameters, either from the first group of operating parameters, or values of another set of operating parameters, in particular at least one additional operating parameter, are taken into consideration in order to determine the volume flow rate and the pressure difference across the pump.

15 Claims, 2 Drawing Sheets

(52) U.S. Cl.
CPC ............. *A61M 1/122* (2014.02); *A61M 1/101* (2013.01); *A61M 2205/3334* (2013.01)

(58) Field of Classification Search
USPC ..................................................... 600/16–18
See application file for complete search history.

(56) References Cited

U.S. PATENT DOCUMENTS

| | | |
|---|---|---|
| 6,634,224 B1 | 10/2003 | Schöb et al. |
| 2014/0357937 A1 | 12/2014 | Reyes et al. |

* cited by examiner

PUMP, AND METHOD FOR OPERATING A PUMP FOR FLUIDS

CROSS-REFERENCE TO RELATED APPLICATIONS

This application is a 371 nationalization of international patent application PCT/EP2016/058039 filed Apr. 12, 2016, the entire contents of which are hereby incorporated by reference, which in turn claims priority under 35 USC § 119 to European patent application EP 15 163 311.2 filed on Apr. 13, 2015.

TECHNICAL FIELD

The invention lies in the field of mechanical engineering and electrical engineering and can be used advantageously in particular in the field of medical technology. In particular, the invention relates to a pump for fluids in the medical field, wherein the volume throughput of the pump and/or a pressure difference generated by the pump are/is detected during operation.

DETAILED DESCRIPTION

Figure 1:
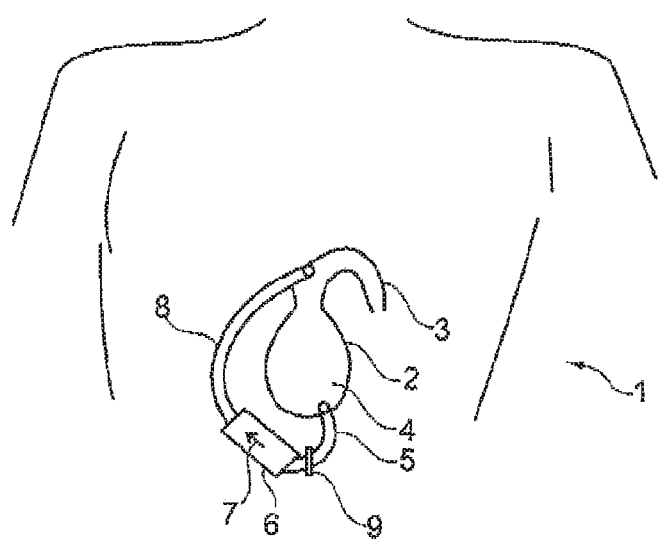
FIG. 1 a schematic view of a patient's body with the heart of the patient and a VAD (ventricular assist device) pump.

In the medical field, fluid pumps are used for different purposes: on the one hand for conveying bodily fluids, in particular for example blood, and on the other hand for conveying fluids foreign to the body, for example pharmaceutically active fluids, which are to be conveyed within, to, or from a patient's body. Particularly for blood pumps, which convey blood within the patient's body or also partially outside the patient's body and which in particular are used as VAD (ventricular assist device) pumps, high demands are placed on the control and management so as to be able to measure or set a volume throughput of the pump and/or a pressure difference with maximum accuracy and reliability.

Usually, for VAD blood pumps, which can convey the blood for example from the left ventricle into the aorta, or also for other blood pumps, for example RVAD pumps, the volume throughput can be determined from the speed of a pump rotor and the pressure difference across the pump on the basis of a performance map of the pump. Experience has shown, however, that a performance map, which usually links values of two or more operating parameters with one another, cannot be used with the same accuracy and reliability for the entire range of use of a pump of this kind.

In this context, various methods are known in principle for determining the volume throughput of a pump or the pressure difference from various sets of operating parameters.

Against the background of the prior art, the object of the present invention is to enable during operation a reliable determination of one or more further operating parameters, in particular the volume flow rate of the pump, over the greatest possible range of possible operating parameters.

Claim 10 characterises a method according to the invention for determining characteristic curves of the pump, and independent claim 11 relates to a pump according to the invention with means for detecting specific operating parameters. Claims 12 to 15 describe embodiments of the pump.

Accordingly, the invention firstly relates to a method for operating a pump comprising a rotor for conveying fluids, in particular a blood pump, in which the volume flow rate through the pump and in particular the pressure difference across the pump is determined, wherein at least one first operating parameter and in particular a second operating parameter of a first group of operating parameters are detected and, depending on the value of the first and in particular also the value of a second operating parameter of the first group, the volume flow rate through the pump and in particular the pressure difference is determined from detected values of the operating parameters, either from the first group of operating parameters, or values of another set of operating parameters, in particular at least one additional operating parameter, are taken into consideration in order to determine the volume flow rate and in particular the pressure difference.

The concept of the invention is based on the fact that, with a pump of the specified type, a number of different methods can be used in order to determine the volume flow rate through the pump and in particular the pressure difference across the pump. Here, the values of operating parameters of the pump are divided in such a way that, for specific values of selected operating parameters, a first method is used to determine the volume flow rate and in particular the pressure difference, and, for other values of operating parameters, a different method is used for determining the volume flow rate and in particular the pressure difference with use of an additional operating parameter. There is thus a division of a performance map of the pump in accordance with specific values of the operating parameters, wherein different determination methods can be used for different regions of the performance map. Thus, for example the most sensitive method or the method for which the required values of the operating parameters can be detected most easily can be used for any region of the performance map under consideration of different sets of operating parameters, which may intersect one another.

To this end, a second method for determining the volume flow rate and/or the pressure difference across the pump can be provided so that an additional operating parameter, not taken into consideration in a first method, is taken into consideration. Here, it can be provided that in the second method all operating parameters which are also taken into consideration in the first method are taken into consideration, or that only some, or even none of the operating parameters taken into consideration in the first method are taken into consideration. It is important that the operating parameters taken into consideration in the first and the second method for determining the volume flow rate and/or the pressure difference differ in terms of at least one operating parameter.

It is also conceivable, in further regions of the performance map, to use additional methods which again take into consideration operating parameters different from those taken into consideration in the first and the second method.

It can additionally also be provided to use a plurality of methods simultaneously in certain regions of the performance map so as to adjust to one another the values thus determined and possibly differing slightly from one another, and thus minimise the error of the calculation.

An advantageous embodiment of the invention provides that the first group of operating parameters contains the detected speed of the pump. The speed of the pump, in the case of a rotor pump, is in principle a meaningful variable for determining the volume flow rate.

It can additionally be provided advantageously that the first group of operating parameters contains the detected pressure difference across the rotor. Here, it can be provided in particular that the first group of operating parameters contains the detected force on a rotor bearing, in particular an axial bearing of the pump (bearing stress).

The volume flow rate through the pump can usually also be reliably determined in a large range of the operating states by detecting the speed and pressure difference across the pump, i.e. the difference in pressure before the pump at the pump inlet and after the pump at the pump outlet.

In many cases, a rotor pump is used as a pump, the rotor of which conveys the fluid in an axial direction. An axial force acting on the rotor and absorbed in a corresponding axial bearing is created as reaction force of the conveyed fluid. The axial force acting on this bearing can be detected in many cases and used as a basis for determining the pressure difference across the pump.

In particular, magnetic axial bearings are often used for medical pumps, on the one hand in order to minimise the friction, and on the other hand in order to produce as little abrasion as possible and additionally cause minimal damage to the molecules of the conveyed organic fluid by mechanical action. In magnetic bearings of this type, the acting axial force can be determined in a simple manner by measuring the force acting in the magnets. In particular in the case of controlled magnetic bearings, the position of the rotor is usually detected and controlled in such a way that the magnetic axial force in the bearing is produced by means of a current of a stationary electromagnet as a counterforce of the axial loading of the rotor. The rotor position can be determined in a simple manner by measuring the voltage induced in the eddy current sensor. This voltage of the eddy current sensor is thus a variable representing the axial force on the rotor and therefore the pressure difference across the rotor.

A particular embodiment of the invention can provide that only the speed of the pump and the axial force on the pump rotor are used in order to decide which operating parameters are taken into consideration in order to determine the volume flow rate through the pump.

In a particular design, the temperature of the conveyed fluid can additionally be used.

It can also be provided advantageously that the first group of operating parameters contains: the temperature of the fluid and/or the absolute pressure of the fluid before or after the pump and/or the torque acting on the rotor of the pump, which torque is determined in particular by means of a variable representing the feed current of an electric motor driving the rotor.

Thus, for example the speed of the rotor, the axial force on the rotor, and the torque acting on the rotor can also be used as operating parameters in order to decide which measurement method is used for the determination of the volume flow rate and which operating parameters are taken into consideration for this purpose.

Another variant can provide that the speed of the rotor, the axial force on the rotor, and an absolute pressure value of the fluid before or after the pump are used in order to decide which operating parameters are taken into consideration.

The aforesaid two variants of the invention can also provide, for example, that in each case the aforesaid operating parameters are used exclusively in order to decide which measurement method is applied, and that the aforesaid parameters are also used exclusively for performing the determination of the volume throughput.

A further advantageous embodiment of the invention provides that an additional parameter is provided by the absolute pressure of the fluid before or after the pump and/or the torque acting on the rotor of the pump, which in particular is determined by means of a variable representing the phase current of an electric motor driving the rotor, in particular a BLDC motor (brushless DC motor).

Depending on which operating parameters are taken into consideration in the first determination method, a further operating parameter not taken into consideration in the first measurement method can be taken into consideration for the determination method different from the first determination method. The weaknesses of the first determination method can thus be compensated in the corresponding region of the performance map by consideration of at least one additional operating parameter, wherein at the same time another operating parameter can also be omitted in the evaluation.

An additional operating parameter of this kind can also be, for example, the temperature of the fluid to be conveyed.

In a specific embodiment of the invention, it can be provided, for example that the pressure difference across the rotor (in particular represented by the detected bearing position) and the speed of the pump are detected and, depending on at least one of the detected values, the volume flow rate through the pump either is determined from the detected values of these two operating parameters, or the detected value of the rotor torque and/or an absolute pressure of the fluid before or after the pump are/is taken into consideration additionally or instead of the pressure difference across the rotor in order to determine the volume flow rate and in particular the pressure difference across the pump.

A further advantageous embodiment of the invention can provide that the volume flow rate through the pump and/or the pressure difference across the pump are/is determined for an operating state both with and without consideration of one or more additional operating parameters or on the basis of a first and a second set of operating parameters, and that the values determined in this way are compared and, from the difference, a correction of the values is determined.

Disturbances of the determined values can be detected from the difference, in particular the pressure differences across the pump determined by the two determination methods. For example, the detection of the axial force acting on the rotor allows a more direct determination of the pressure difference than the theoretical calculation from the speed and an absolute hydrostatic pressure value or from the speed and the torque acting on the rotor. Disturbances or changes in the pump, for example specific transient operating states or blockages, build-ups or the like, for example also deformations of the pump rotor, can be identified by the difference of the results of the two determination methods.

The method according to the invention can therefore provide that the pressure difference across the pump is determined on the one hand by the detection of an axial force on a rotor bearing or an axial position shift of the rotor against a bearing force and on the other hand by means of the measured speed of the rotor and a measured absolute pressure of the fluid before or after the pump and/or the torque acting on the rotor, and that unstable flow states in the pump or geometrical changes, for example caused by deposits, are detected by a determined difference between the values of the pressure difference thus determined.

The invention relates not only to an operating method that uses different methods for determining the aforesaid operating parameters of the pump depending on the region of the performance map in which the pump is operated, but also to a method for determining the corresponding characteristic curves or performance maps. In this regard, the invention relates to a method for operating a pump comprising a rotor for conveying fluids, in particular a blood pump, in which the volume flow rate through the pump and in particular the pressure difference across the pump is determined, wherein the speed of the rotor, a force acting on an axial bearing of the rotor, and an absolute pressure of the fluid before or after the pump and/or the torque acting on the rotor of the pump, which torque is determined in particular by means of a variable representing the phase current of an electric motor driving the rotor, are detected in order to determine characteristic curves of the pump.

In principle, when determining the performance map, more operating parameters than would be necessary in order to determine the volume throughput of the pump and/or the pressure difference in a specific performance map region are detected. Due to the wide-ranging selection of input parameters for the performance map determination, the use of different determination methods is possible depending on the region of the performance map in which the current operating state of the pump is currently located.

In addition, the invention also relates to a pump that enables or implements the above-described operating methods. The subject matter of the invention is thus, inter alia, a pump comprising a rotor for conveying fluids, in particular a blood pump, having a means for detecting the speed of the rotor, a means for detecting the pressure difference across the rotor, in particular by detecting a force acting on an axial bearing of the rotor, a means for detecting an absolute pressure at the inlet or outlet of the pump, and in particular a means for detecting the torque acting on the rotor, in particular by detecting a variable representative of the phase current of an electric motor driving the rotor (phase current of a BLDC motor).

The invention will be shown hereinafter in figures of a drawing and explained below on the basis of exemplary embodiments.

FIG. 1 shows the upper body of a patient 1 with the heart 2 of the patient and part of the aorta 3. An inlet connector 5 of a VAD pump 6 is connected to a ventricle 4 of the heart, the pump suctioning blood from the ventricle 4 in the direction of the arrow 7 and conveys the blood directly into the aorta 3 via the outlet cannula 8.

Pumps of this kind can fundamentally support the pumping function of a heart that is poorly or that is not able to work at full capacity. This can be provided as temporary therapy or as on-going therapy. Here, the use of axial rotor pumps that convey blood in an axial direction 7 by means of a quickly rotating rotor in the pump housing has proven to be particularly advantageous. Pumps of this kind are usually driven by an electric-motor drive in the region of the pump housing, which drive can be fed by a portable battery or a stationary power connection.

So as to be able to monitor the state of health of the patient and also the operating state of the pump sufficiently accurately, it is necessary to determine and track the volume throughput through the pump. To this end, different methods are known in principle, in which for example the speed of the rotor and the pressure difference across the rotor are detected. It is also possible to determine the volume flow rate by means of the speed of the pump and the measurement of the stationary pressure of the blood to be conveyed by means of an absolute pressure sensor 9 on the pump. Lastly, the volume throughput can also be determined by means of an approach in which the speed of the pump rotor and the torque acting on the rotor are taken into consideration.

In all of these methods the volume flow rate and/or the pressure difference across the pump are/is usually determined by means of performance maps from the detected measured values for the operating parameters constituted by speed of the rotor, pressure difference across the rotor or axial position shift of the rotor against a bearing force, torque of the rotor, and absolute pressure in the region of the pump.

Figure 2:
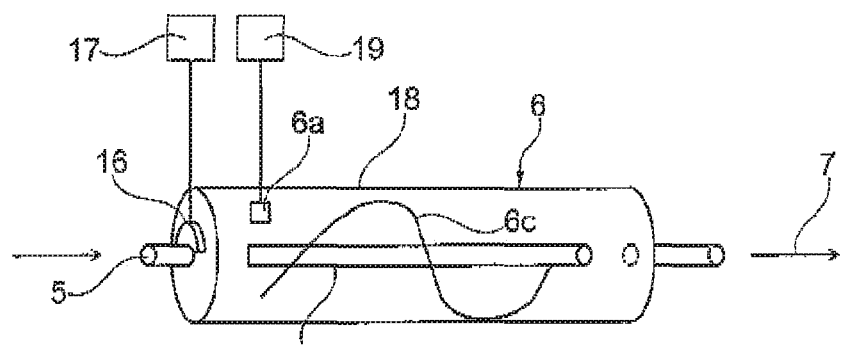
FIG. 2 a three-dimensional schematic view of an axial rotor pump.

FIG. 2 schematically shows an axial pump 6 with a rotor 6b mounted in a housing 6a, which rotor has one or more conveying elements 6c, for example in the form of a peripheral helical conveying blade. By rotating the rotor, the fluid to be conveyed or the blood is conveyed in the housing 6a in the direction of the arrow 7.

Figure 3:
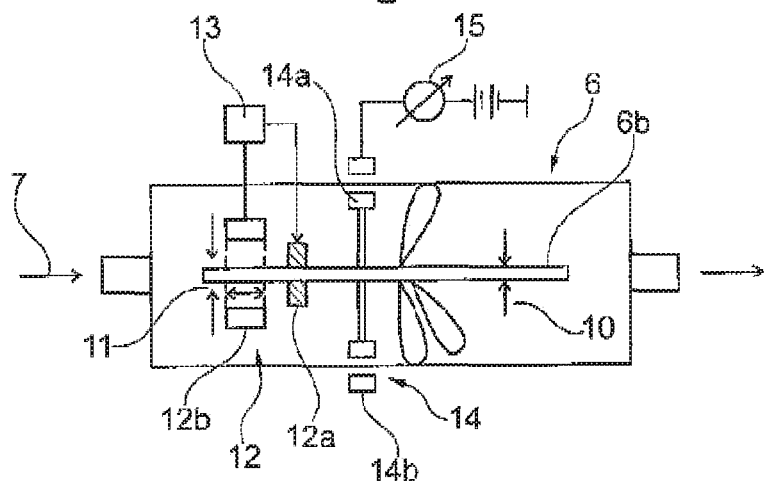
FIG. 3 a schematic side view showing a housing of an axial pump with a rotor, a drive, and a magnetic axial bearing.

The mounting and the drive of the rotor of the pump 6 are illustrated in greater detail in FIG. 3. Firstly, a first radial bearing is illustrated symbolically in the region of the rotor 6b and is denoted by reference sign 10, whereas a second radial bearing 11 is also illustrated symbolically and is denoted by 11. The second radial bearing 11 can be combined for example with a magnetic axial bearing 12, but can also be constructed separately therefrom.

The axial bearing 12 is formed as an adjustable magnetic axial bearing, wherein a first annular magnet 12a is connected to the rotor 6b and rotates therewith.

A second annular magnet or an annular arrangement of individual magnets 12b is arranged in a stationary manner in the housing 6a of the pump 6 and surrounds the rotor 6b. By repulsion from the stationary magnet 12b or the stationary magnet arrangement 12b on the one hand and the rotating magnet 12a on the rotor 6b, an axial force acting on the rotor is received, which force, as reaction force, is directed oppositely to the flow 7 of the fluid through the pump.

The axial bearing 12 has a sensor for detecting the axial position of the magnet 12a fixed to the hub, wherein the information regarding the axial position is communicated to a control means 13. The control loop of the magnetic bearing 12 can thus be closed, and the control means 13 can control the axial position of the magnet 12a and therefore of the rotor 6b to a constant quantity. The force received here by the axial bearing can be determined in some cases on the basis of the current strength applied by the control means 13.

The force received by the axial bearing can be determined in the case of an unregulated bearing for example by measuring the axial deflection of the rotor against a magnetic force of the axial bearing. The rotor position can be determined by means of a "bearing stress", which is arises due to the eddy current sensors that react sensitively in respect of the axial distance from stationary magnets.

An electric motor 14 which for example can provide permanent magnets 14a, which are fixedly connected to the rotor, and a stator 14b, which is connected to the pump housing 6a, is additionally illustrated in FIG. 3. By suitable actuation of stator windings, a brushless electric motor is thus provided. The current strength with which the stator 14*b* is acted on can be detected by means of a measuring unit 15, and from this current strength it is possible to determine the generated torque on the rotor in a simple manner.

Coming back to FIG. 2, it should be mentioned that a hydrostatic pressure sensor 16 is illustrated there at the pump inlet connector 5 and is connected to a corresponding processing means 17. In addition, a temperature sensor 18 is additionally illustrated within the pump housing 6*a* in FIG. 2 and is likewise connected to a processing means 19. The temperature sensor 18 can also be arranged outside the pump in a region through which the conveyed fluid is passed.

Figure 4:
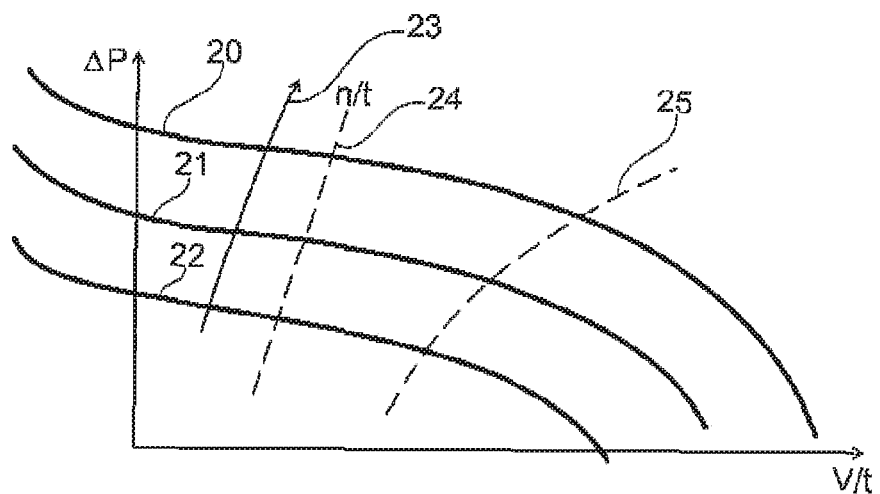
FIG. 4 a graph of a typical performance map of a pump with characteristic curves which enable an association of a speed and a pressure difference with a volume flow rate.

FIG. 4 shows a graph in which the volume flow rate through the pump is plotted on the horizontal axis in volume per unit of time against the pressure difference across the pump for different speeds of the pump. This results in a performance map in which, for example, three characteristic curves 20, 21, 22 for different speeds are illustrated. The arrow 23 thus shows, generally, the direction of transition between curves of different speeds.

Operating points of the pump (pressure difference between inlet and outlet of the pump and the volume flow rate conveyed through the pump) for different speeds of the pump are thus illustrated in the form of characteristic curves. Here, the speed and the axial bearing position of the rotor have been plotted in each case as representative variable for the pressure difference across the rotor in order to determine the characteristic curve. Measurement points of characteristic curves can be interpolated by corresponding regression curves. During operation of the pump, the volume flow rate through the pump can thus be determined from the speed and the axial bearing position of the rotor.

Since it has been found that for specific pump types there are regions in the performance map in which the association between the bearing position/pressure difference and the volume flow rate at known speed is unclear or is at least hazy, another method was selected for specific regions of the performance map in order to determine the volume flow rate. The appropriate determination method can thus be selected depending on the region of the performance map in which the operating point of the pump is located, i.e. for example depending on the speed and/or the pressure difference across the pump.

By way of example, a sub-map of the performance map in which the volume flow rate is not determined from the speed and the pressure difference across the rotor or at least not from these parameters alone is formed in FIG. 4 between the two dashed lines 24 and 25. For example, the torque of the rotor, determined by the current of the electric drive motor of the rotor, and/or the absolute pressure at the inlet or outlet of the pump can be taken into consideration in the map between the lines 24 and 25. These variables can be evaluated alone or in combination with the speed; however, the bearing position can additionally also be included in the determination of the volume flow rate as indicator for the pressure difference across the rotor.

Figure 5:
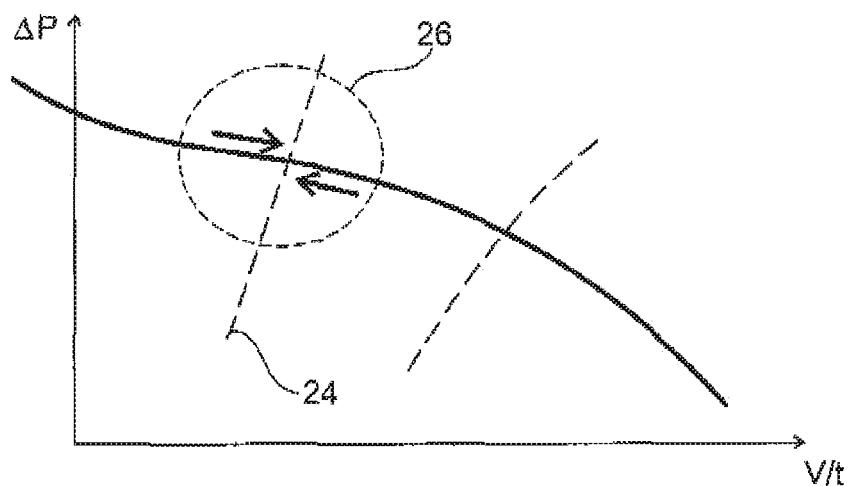
FIG. 5 a graph according to FIG. 4, on the basis of which a determination of the pressure difference across the pump on the basis of two different methods and the comparison of the results is explained.

FIG. 5 shows the use of a plurality of measurement methods in a boundary region/transition region of the performance map indicated by the dashed circle 26. This region lies in the vicinity of the partition line 24 between the two regions of the performance map that require different measurement methods for the determination of the volume flow rate. In the region around the partition line 24, the volume flow rate or the pressure difference across the pump can then be determined for example by different methods using different detected operating parameters. If the values for example of the pressure difference across the pump thus determined are different, this can be indicative of changes in the pump, for example by blockages, build-ups, deformations, or unstable flow states. The detection of such phenomena is particularly important during operation of a blood pump so as to rule out any endangerment to the patient.

The invention, besides relating to a method for operating a pump of this kind and for determining the volume flow rate in different performance map regions, also relates to a method for determining a corresponding performance map by using different operating parameters in different regions of the performance map.

In addition, the invention also relates to a pump which has corresponding means for detecting the necessary operating parameters.

By means of the invention, the determination of the volume flow rate through a pump is significantly improved, in particular for pumps for which a single measurement method or the orientation along specific characteristic curves over the entire performance map is not sufficient for design reasons.

The invention claimed is:

1. A method for operating a pump comprising a rotor for conveying fluids, the method comprising:
   detecting a value of at least one first operating parameter of a first group of operating parameters of the pump; and
   determining a volume flow rate through the pump and/or a pressure difference across the pump, wherein, depending on the value of the at least one first operating parameter of the first group, the volume flow rate through the pump and/or the pressure difference across the pump is determined from either detected values of the first group of operating parameters or detected values of a second group of operating parameters,
   wherein the volume flow rate through the pump and/or the pressure difference across the pump is determined for an operating state both with and without consideration of one or more additional operating parameters, and wherein a difference in the values of the volume flow rate and/or the pressure difference thus determined is calculated, and a correction of the values is determined from the difference.

2. The method according to claim 1, wherein the first group of operating parameters includes a detected speed of the pump.

3. The method according to claim 1, wherein the first group of operating parameters includes a detected pressure difference across the rotor.

4. The method according to claim 1, wherein the first group of operating parameters includes a detected force on a rotor bearing, in particular an axial bearing of the pump.

5. The method according to claim 1, wherein the first group of operating parameters includes: a temperature of the fluid and/or an absolute pressure of the fluid before or after the pump and/or a torque acting on the rotor of the pump.

6. The method of claim 5, wherein the first group of operating parameters includes: a temperature of the fluid, an absolute pressure of the fluid before entering or after exiting the pump, and/or a torque acting on the rotor of the pump.

7. The method of claim 5, wherein the torque acting on the rotor of the pump is determined by a means of a variable representing a phase current of an electric motor driving the rotor.

8. The method according to claim 1, wherein the second group of operating parameters includes an absolute pressure of the fluid before entering or after exiting the pump, and/or a torque acting on the rotor of the pump.

9. The method according to claim 1, wherein a pressure difference across the rotor and a speed of the pump is detected and, depending on at least one of the detected values of the volume flow rate through the pump, is either determined from the detected values of these two parameters or from a detected value of a rotor torque and/or an absolute pressure of the liquid before or after the pump is taken into consideration additionally or instead of the pressure difference across the rotor in order to determine the volume flow rate and/or the pressure difference across the pump.

10. The method according to claim 9, wherein the pressure difference across the rotor is represented by a detected bearing position.

11. The method according to claim 1, wherein the pressure difference across the pump is determined 1) from an axial force on a rotor bearing or an axial position shift of the rotor against a force and 2) from a measured speed of the rotor and a measured pressure of the fluid before or after the pump, and/or a torque acting on the rotor, and wherein unstable flow states in the pump or geometrical changes are detected by a determined difference between the two values of the pressure difference thus determined.

12. The method of claim 1 wherein a speed of the rotor, a force acting on an axial bearing of the rotor, an axial position shift of the rotor against a force and an absolute pressure of the fluid before or after the pump, and/or a torque acting on the rotor of the pump are detected in order to determine characteristic curves of the pump from which the volume flow rate through the pump and/or the pressure difference across the pump is determined.

13. A method for operating a pump comprising a rotor for conveying fluids, the method comprising:
   detecting a value of at least one first operating parameter of a first group of operating parameters of the pump; and
   determining a volume flow rate through the pump and/or a pressure difference across the pump, wherein, depending on the value of the at least one first operating parameter of the first group, the volume flow rate through the pump and/or the pressure difference across the pump is determined from either detected values of the first group of operating parameters or detected values of a second group of operating parameters,
   wherein a pressure difference across the rotor and a speed of the pump is detected and, depending on at least one of the detected values of the volume flow rate through the pump, is either determined from the detected values of these two parameters or from a detected value of a rotor torque and/or an absolute pressure of the liquid before or after the pump is taken into consideration additionally or instead of the pressure difference across the rotor in order to determine the volume flow rate and/or the pressure difference across the pump.

14. The method according to claim 13, wherein the pressure difference across the rotor is represented by a detected bearing position.

15. A method for operating a pump comprising a rotor for conveying fluids, the method comprising:
   detecting a value of at least one first operating parameter of a first group of operating parameters of the pump; and
   determining a volume flow rate through the pump and/or a pressure difference across the pump, wherein, depending on the value of the at least one first operating parameter of the first group, the volume flow rate through the pump and/or the pressure difference across the pump is determined from either detected values of the first group of operating parameters or detected values of a second group of operating parameters,
   wherein the first group of operating parameters includes: a temperature of the fluid and/or an absolute pressure of the fluid before or after the pump and/or a torque acting on the rotor of the pump,
   wherein the torque acting on the rotor of the pump is determined by a means of a variable representing a phase current of an electric motor driving the rotor.

* * * * *